United States Patent [19]

Cadwell

[11] Patent Number: 4,994,015

[45] Date of Patent: Feb. 19, 1991

[54] MAGNETIC STIMULATOR COILS

[75] Inventor: John A. Cadwell, Kennewick, Wash.

[73] Assignee: Cadwell Industries, Inc., Kennewick, Wash.

[21] Appl. No.: 309,915

[22] Filed: Feb. 10, 1989

Related U.S. Application Data

[63] Continuation of Ser. No. 95,957, Sep. 14, 1987, abandoned.

[51] Int. Cl.$^5$ .............................................. A61N 2/02
[52] U.S. Cl. ..................................... 600/13; 335/299; 336/225; 336/228
[58] Field of Search ................... 600/9, 10, 11, 12, 13, 600/15; 335/299; 128/419 F, 804; 336/225, 227, 228

[56] References Cited

U.S. PATENT DOCUMENTS 1,624,397  4/1927  Dequer .................................. 128/1.5
2,831,136  6/1954  Hanlet .................................. 335/299
4,412,540  11/1983 Bentall ................................. 128/422
4,501,265  2/1985  Pescatore ........................... 128/419 F

FOREIGN PATENT DOCUMENTS

0051997  8/1936  Denmark ............................... 600/15

Primary Examiner—Lee S. Cohen
Assistant Examiner—K. M. Pfaffle
Attorney, Agent, or Firm—Christensen, O'Connor, Johnson & Kindness

[57] ABSTRACT

Magnetic stimulator coils having a definable region wherein magnetic field intensity is greater than at other regions of the coil are disclosed. The definable region is formed by one or more corners in a coil and/or by a higher concentration of windings in one region of the coil. Because the magnetic field produced at the definable region of the windings is higher than at other regions, the location where stimulation is to occur is better defined when the definable region of a coil formed in accordance with the invention is suitably positioned on the skin of a patient and energized by a suitable power source. Preferably, the windings are splayed because splayed winding stimulator coils are more efficient than concentrated winding stimulator coils. Efficiency is better because magnetic field intensity is reduced where windings are splayed due to a reduction in mutual inductance. A less intense magnetic field results in the need for less power to create the desired magnetic field in the region where the windings are more concentrated.

9 Claims, 7 Drawing Sheets

MAGNETIC STIMULATOR COILS

This application is a continuation application based on prior copending application Ser. No. 07/095,957, filed on Sept. 14, 1987 now abandoned.

TECHNICAL AREA

This invention relates to neuron stimulation and, more particularly, magnetic coils for neuron stimulators.

BACKGROUND OF THE INVENTION

In recent years, methods and apparatus for creating evoked potentials in the neural pathways of higher level organisms (e.g., animals and humans) have been developed. Evoked potentials can produce observable movements and/or analyzable electric signals (e.g., brain waves). Evoked potentials are created by stimulating neural pathways. In the past, three major types of stimulators have been used to create evoked potentials— light, sound and electrical stimulators. Light and sound stimulators have been used to stimulate the sensory and neural pathways associated with the eyes and ears. Electric stimulators have been used to stimulate motor neural pathways and the sensory neural pathways associated with somatic sensations, i.e., sensations associated with the sense of touch. The present invention is directed to electric stimulation.

In the past, the most common way to electrically stimulate motor and somato sensory neural pathways has been to attach a pair of spaced-apart electrodes to the body at the stimulus location. When an electric potential is applied to the electrodes, a current flow through the body is created. The current flow produces an electric field that disrupts the polarization of neurons located in the field (commonly called depolarization of the neurons) causing an evoked potential "message" to be transmitted along the neural pathway formed by depolarized and other neurons that define the neural pathway.

While electric stimulation using a pair of spaced-apart electrodes has certain advantages, it also has several disadvantages. In order to overcome certain of these disadvantages, in particular, the shallow penetration of electrode stimulators, magnetic stimulators have been developed. As described in U.S. Pat. application Ser. No. 008,210 entitled "Method and Apparatus for Magnetically Stimulating Neurons," filed Jan. 28, 1987, now U.S. Pat. No. 4,940,453, and assigned to the assignee of the present application, magnetic stimulators have the advantage of being noncontacting, relatively pain-free and capable of stimulating deep, normally inaccessible, nerves.

In the past, magnetic stimulators have stimulated neural pathways by energizing a pancake-shaped coil placed flat on the skin of a patient overlying the neural pathway to be stimulated. The energized coil creates a magnetic field that depolarized the neurons underlying the stimulation site. In comparison with electrode stimulators, one disadvantage of using pancake-shaped coils placed flat on the skin of a patient to stimulate neural pathways is a lack of stimulation site accuracy. More specifically, even though electrode stimulators have other disadvantages, when compared to magnetic stimulators, electrode stimulators are more accurate since the stimulating field produced by the electrodes is more confined than is the stimulating field produced by pancake-shaped magnetic coils placed flat on the skin of a patient. This invention is directed to magnetic stimulator coils that overcome this disadvantage.

One major disadvantage of magnetic stimulators is their large power requirements. More specifically, the relatively high voltage and current required by magnetic stimulators to produce a depolarizing magnetic field necessitate that magnetic stimulators have large power supplies. Part of the reason for the high voltage and current requirement is the lack of efficiency of the coils used in the past to create magnetic stimulation. This invention is also directed to providing magnetic stimulator coils that are more efficient than magnetic stimulator coils used in the past.

SUMMARY OF THE INVENTION

In accordance with this invention, a magnetic stimulator coil that produces a magnetic field intensity in a definable region of the coil that is greater than the magnetic field intensity in other regions of the coil, when an electric current passes through the coil, is provided. In one form the coil has a corner, preferably sharp, and/or splayed windings. When suitably powered, the intensity of the magnetic field produced at the corner of the coil is greater than the magnetic field produced in other regions of the coil. The steep or more concentrated magnetic field allows the location of stimulation to be better controlled when the coil is suitably positioned on the skin of a patient because power can be controlled such that stimulation occurs only where the field is the greatest—under the corner. Splayed winding stimulator coils are more efficient than concentrated windings because the magnetic field is less intense when the windings are splayed due to a reduction in mutual inductance. Less intense fields store less energy and, thus, have a lower drive energy requirement.

In accordance with other aspects of this invention, the angle defined by the corner can be obtuse, or define a right angle, as well as acute, i.e., sharp.

In accordance with further aspects of this invention, the coil has a petal shape, the apex of the petal defining the sharp corner.

In accordance with alternative aspects of this invention, the coil has more than one corner. For example, the coil can be rectangularly-shaped, triangularly-shaped or arch-shaped.

In accordance with still other aspects of this invention, the splayed region of the coil is remote from the corner.

In accordance with still further aspects of this invention, the splayed region fans out from the corner.

In accordance with yet still other aspects of this invention, the splayed coil is formed by two lobes, one lying on either side of the corner. As a result, the coil is substantially flat. In this version the definable region occurs where the lobes meet because the greatest magnetic field is produced where the windings are the most concentrated, which is where the lobes meet.

As will be readily appreciated from the foregoing description, the invention provides magnetic stimulator coils that overcome the disadvantages of prior art stimulator coils. Because a concentrated magnetic field having a steep gradient is produced at a definable region by a coil formed in accordance with the invention, the location of stimulation can be better controlled when the coil is suitably positioned on the skin of a patient. The steep, concentrated magnetic field can be defined by a sharp corner in an otherwise circular coil or by a higher concentration of windings. Further, because a magnetic field is less intense where coil windings are splayed, splayed coil embodiments of the invention are more efficient than prior art stimulator coils. More specifically, magnetic coil efficiency is dependent on the amount of energy needed to produce the desired intensity field in the definable region of the coil. The amount of energy used by a coil to produce a magnetic field is related to the mutual inductance of the coil windings. Reducing coil mutual inductance reduces energy requirements. Because splaying windings reduces mutual inductance, splaying windings where high magnetic field strength is not required produces a more efficient coil.

BRIEF DESCRIPTION OF THE DRAWINGS

The foregoing and other features and advantages of the present invention will become more readily appreciated as the same becomes better understood by reference to the following detailed description when taken in conjunction with the accompanying drawings wherein.

DESCRIPTION OF THE PREFERRED EMBODIMENTS

Figure 1:
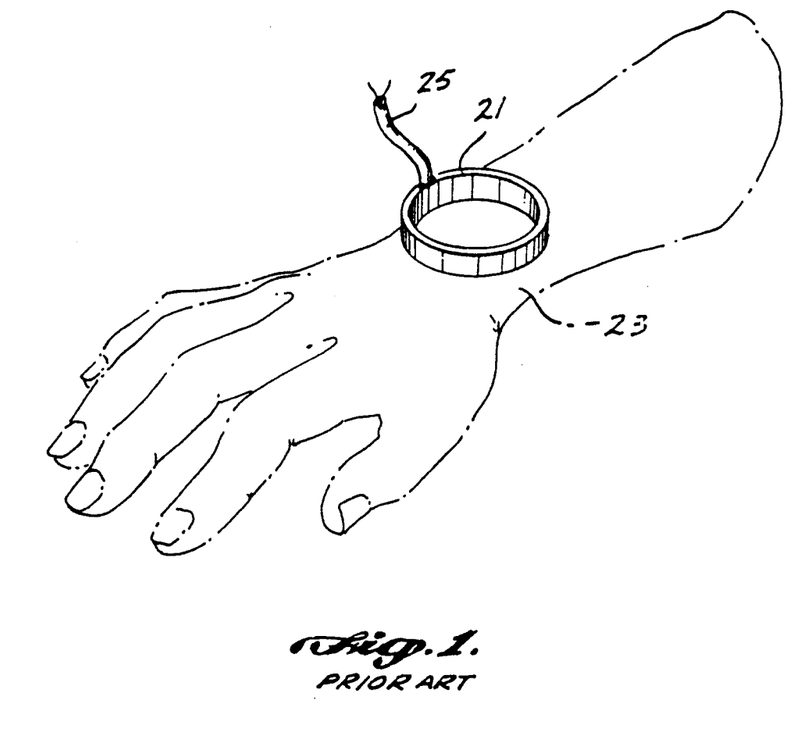
FIG. 1 is a pictorial view illustrating a prior art magnetic stimulator coil positioned on the wrist of a patient's arm in accordance with accepted orientation procedures.

Prior to describing the preferred embodiments of the invention, a brief description of prior magnetic stimulator coils and their disadvantages is set forth. In this regard, FIG. 1 illustrates a prior art magnetic stimulator coil 21 positioned in a conventional manner atop the wrist 23 of a patient. The coil 21 is pancake-shaped, i.e., the coil 26 is both flat and circular. The coil 21 is connected by a cable 25 to the output of a magnetic stimulator (not shown). A suitable magnetic stimulator is described in U.S. patent application Ser. No. 008,210, entitled "Method and Apparatus for Magnetically Stimulating Neurons" filed Jan. 28, 1987, and assigned to the assignee of this application. The subject matter contained in application Ser. No. 008,210 is incorporated herein by reference. When the magnetic stimulator connected by the cable 25 to the coil 21 applies a high voltage, high current pulse to the coil 21, the coil produces a magnetic field that stimulates neurons in the area of the wrist 23 that underlie the coil 21.

While magnetic stimulator coils have a depth of penetration advantage over other types of electrical neuron stimulators, specifically a pair of spaced-apart electrodes, in the past, magnetic stimulator coils have had the disadvantage of being difficult to focus. This difficulty is due to the size and shape of prior magnetic stimulator coils. Because such coils have had a relatively large ($\pm$ 3 inch) diameter, it has been difficult to place the coils in the precise position required to stimulate a desired neural pathway and not stimulate nearby pathways.

Figure 2:
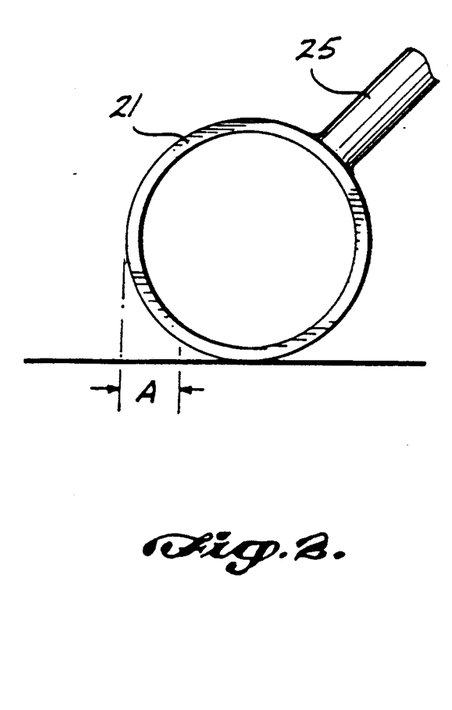
FIG. 2 illustrates a coil of the type shown in FIG. 1 oriented in a different manner.

One potential way of overcoming the focusing difficulty of large pancake-shaped magnetic stimulator coils of the type shown in FIG. 1 is to place the coil on edge rather than flat, as shown in FIG. 2. While such repositioning of the coil 21 improves focusing in one plane, focusing in the plane of the coil is still difficult to ascertain. Thus, the location of depolarizaton in the plane of the coil is difficult to determine. The letter "A" in FIG. 2 denotes the region over which depolarization may occur.

In accordance with this invention, rather than using a pancake-shaped coil having a circular shape defined by windings that create a magnetic field of uniform intensity at all winding locations, coils formed in accordance with the invention produce a nonuniform magnetic field intensity. Specifically, coils formed in accordance with the invention produce a concentrated magnetic field having a steep gradient at one (or more) definable coil locations. In some embodiments of the invention, the definable coil location is created by a corner(s) in an otherwise circular coil. In other embodiments of the invention, the definable coil location is created by forming the coil such that a higher concentration of windings occurs at the definable region.

Figure 3:
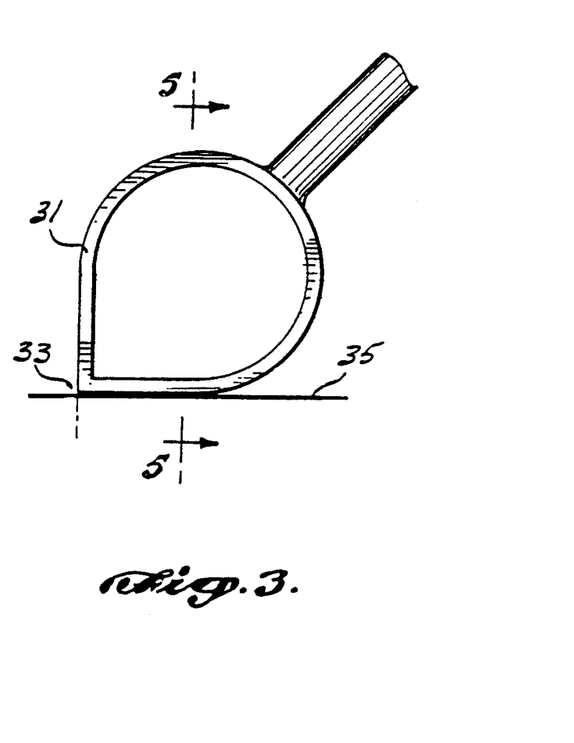
FIG. 3 illustrates a coil formed in accordance with the invention oriented in the manner illustrated in FIG. 2.

The embodiment of the invention illustrated in FIG. 3 includes a single, sharp corner 33 in an otherwise circular coil 31. As a result, the coil is petal-shaped. When the coil 31 is placed on the skin 35 of a patient, preferably oriented edgewise, neuron depolarization occurs beneath the region where the sharp corner 33 of the coil lies when the coil is energized with a high voltage, high current pulse. Neuron depolarization occurs beneath the sharp corner because magnetic flux concentration is higher at the sharp corner 33 than at any other place along the region where the coil 31 rests on the skin 35 of a patient. The coil 31 can also be oriented to lie flat on the surface of the skin 35. In either orientation, the focal point of neuron depolarization is beneath the sharp corner 33.

Figure 4:
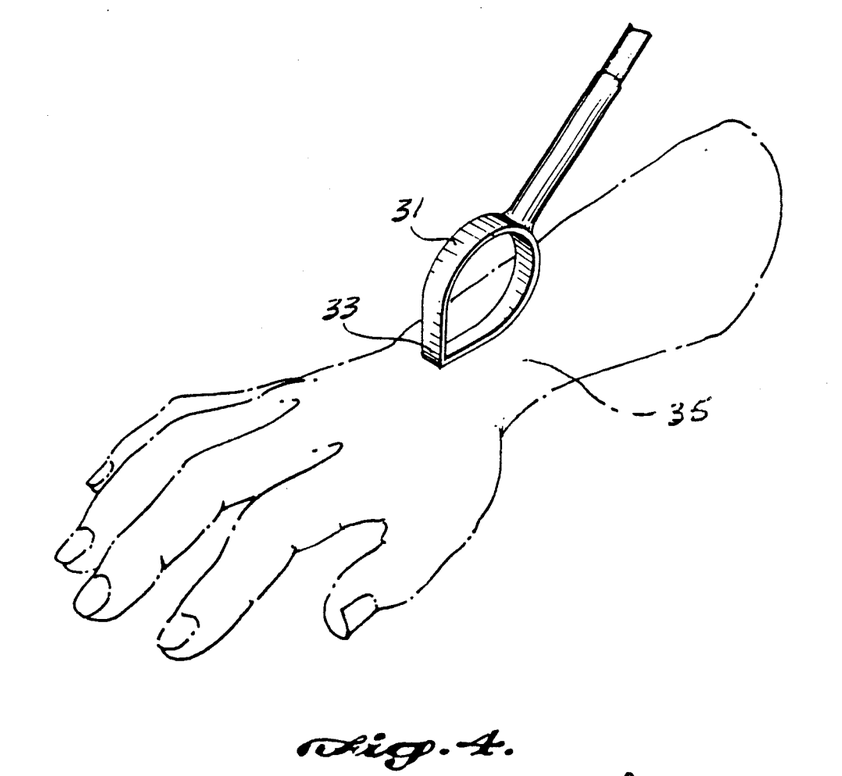
FIG. 4 is a pictorial view illustrating a coil of the type illustrated in FIG. 3 positioned on the wrist of a patient.
Figure 5:
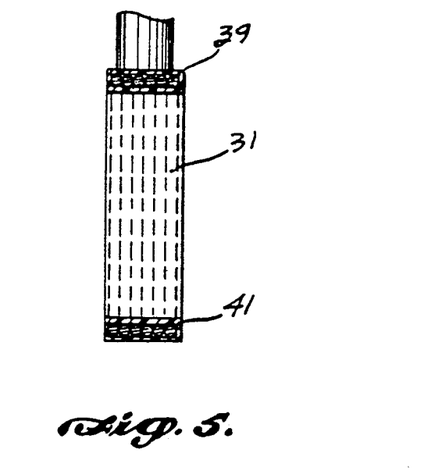
FIG. 5 is an elevational, cross-sectional view of the coil illustrated in FIGS. 3 and 4.

FIG. 4 is a pictorial view illustrating a petal-shaped coil 31 of the type illustrated in FIG. 3 and described above positioned atop the wrist 35 of a patient. Thus, FIG. 4 illustrates a coil formed in accordance with the invention located in the same region of a patient's body as the prior art coil illustrated in FIG. 1. As will be readily apparent from comparing FIGS. 4 and 1 and the foregoing description, the location of depolarization is better defined by a coil formed in accordance with the invention than by the prior art coil. FIG. 5 is a cross-sectional view taken along line 5—5 of FIG. showing the cross-sectional configuration of the coil 31. As illustrated in FIG. 5, the coil 31 may comprise a single layer coil of wire 39 encapsulated by an encapsulating material 41 that adds rigidity to the coil 31.

Figure 6:
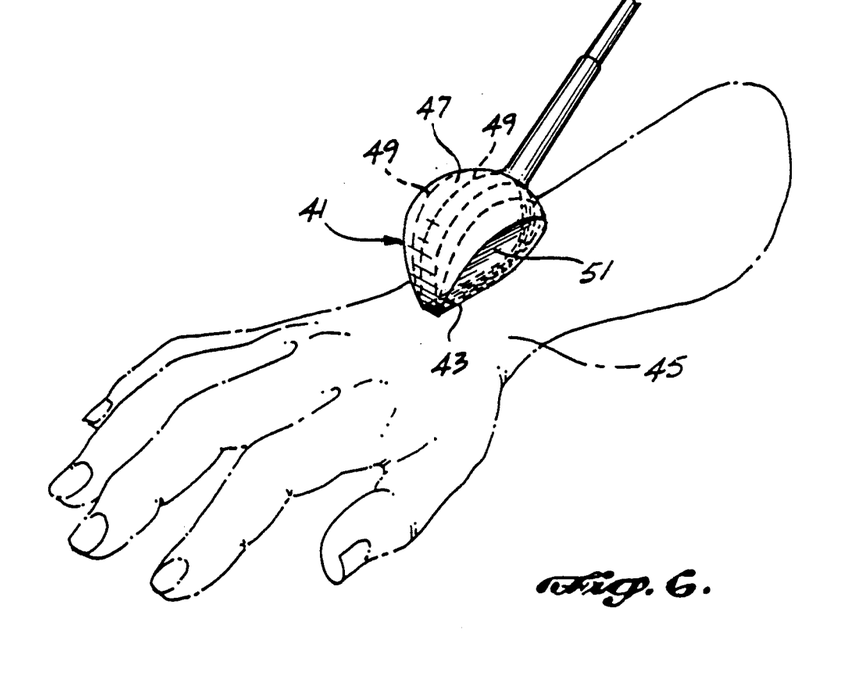
FIG. 6 is a pictorial view of a splayed coil formed in accordance with the invention.
Figure 7:
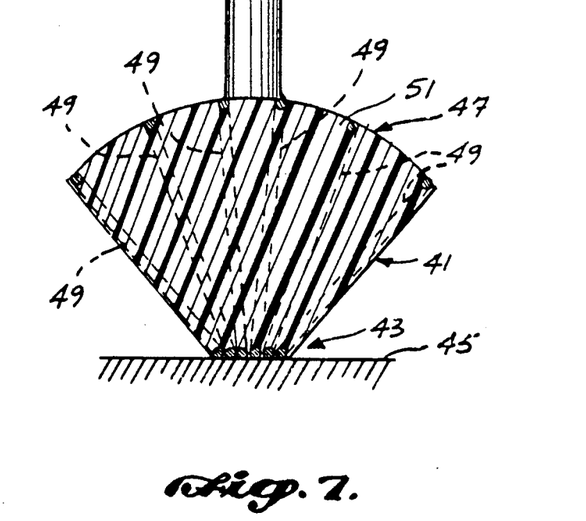
FIG. 7 is a cross-sectional view of the splayed coil illustrated in FIG. 6.

FIGS. 6 and 7 illustrate an additional feature of the invention that may or may not be included in some embodiments. Specifically, FIGS. 6 and 7 illustrate a splayed version of the invention. More specifically, FIGS. 6 and 7 illustrate a magnetic stimulator coil 41 formed in accordance with the invention wherein the region of the coils 43 to be placed on the skin 45 of a patient are concentrated. The region of the coil wires 47 remote from the skin 45 are spaced apart. Thus, the coil is splayed. While somewhat uniform spacing of the splayed coil windings is illustrated in FIGS. 6 and 7, the windings can be nonuniformly spaced, if desired. Preferably, the windings are held in their splayed position by a suitable encapsulation material 51. As will be appreciated by those familiar with magnetic coils, spaced-apart windings have less mutual inductance than concentrated windings. Thus, splayed windings store less energy than closely spaced windings. As a result, less energy is required by a splayed core to create a predetermined magnetic field in the region of the coil that is placed against the skin, i.e., the concentrated winding region of the coil, than is required by a non-splayed coil. Hence, a splayed magnetic stimulator coil is more efficient than is a non-splayed coil. Preferably, the splayed coil illustrated in FIGS. 6 and 7, has a sharp corner, which may be an acute, right, or obtuse angle when viewed from the side.

Figure 8:
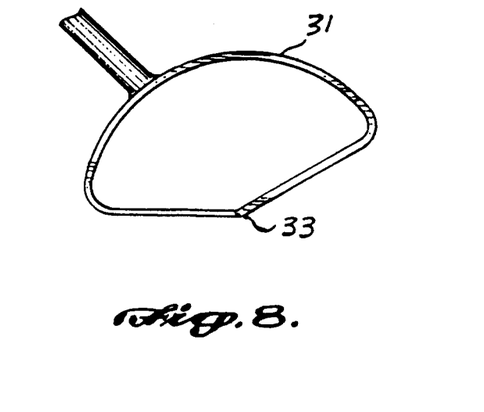
FIGS. 8–11 are plane views of alternative configurations of coils formed in accordance with the invention.
Figure 9:
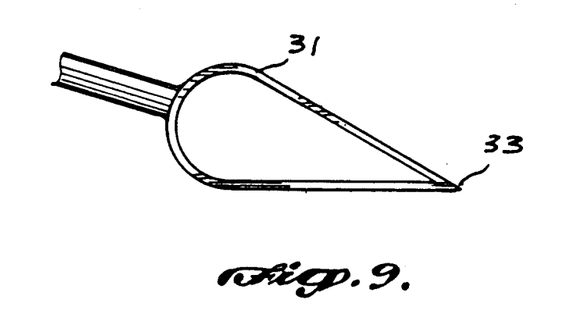
Figure 10:
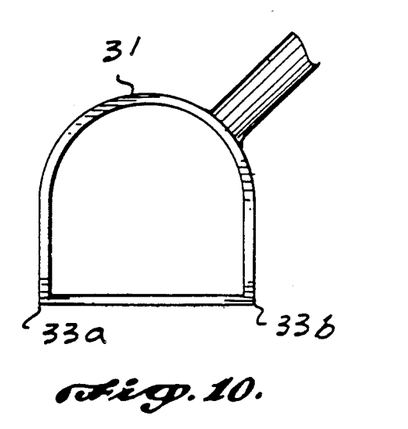
Figure 11:
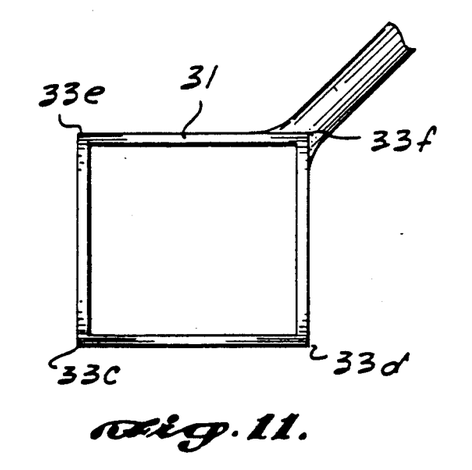
Figure 16:
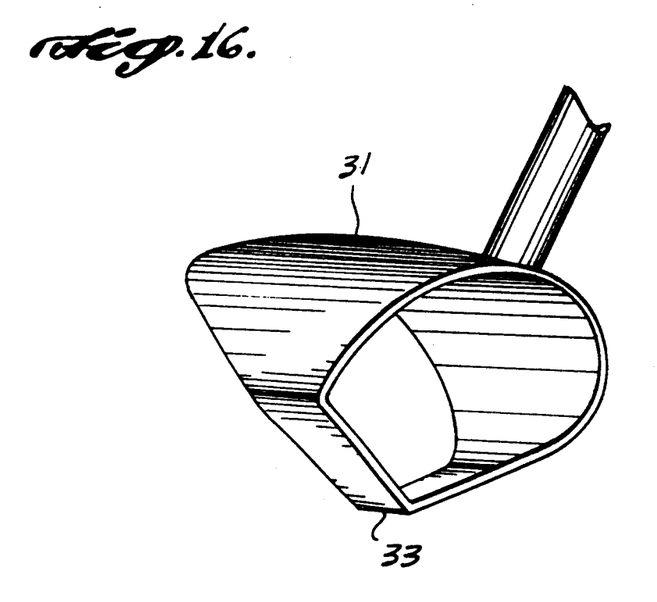
FIGS. 16 and 17 are pictorial views of alternative configurations of the coils illustrated in FIGS. 8 and 9, respectively.
Figure 17:
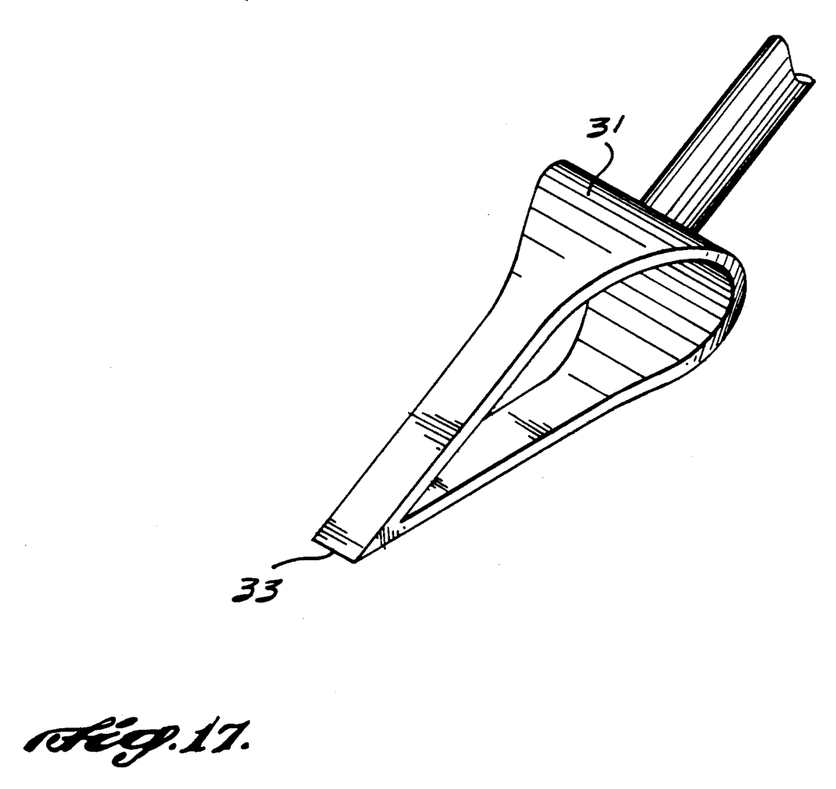

In addition to the corner 33 defining a right angle, as illustrated in FIGS. 3 and 4, the corner 33 can define an obtuse angle, as illustrated in FIGS. 8 and 16 or an acute angle as illustrated in FIGS. 9 and 17. Still further, in addition to defining a single corner 33, the coil may define more than one corner. In this regard, FIG. 10 illustrates an arch-shaped embodiment of the invention that includes two corners 33a and 33b; and, FIG. 11 illustrates a rectangular coil formed in accordance with the invention that includes four corners, 33c, 33d, 33e and 33f. As with the single corner embodiments of the invention, because magnetic field intensity is highest at the corners of the coils illustrated in FIGS. 10 and 11, the region underlying the corners is where neuron depolarization occurs when the corners are placed against the body of a patient.

Figure 12:
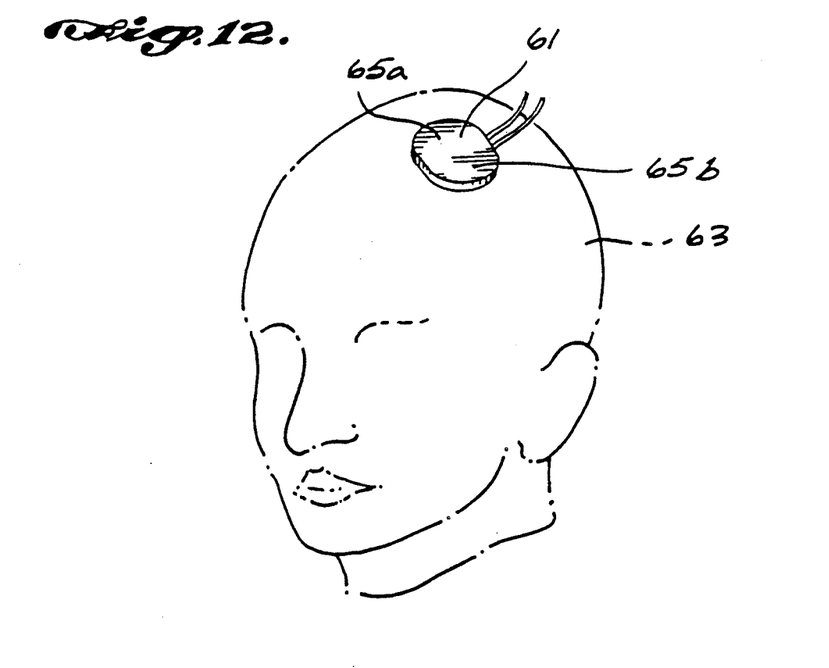
FIG. 12 is a pictorial view of a further embodiment of the invention positioned on the cranium of a patient.
Figure 13:
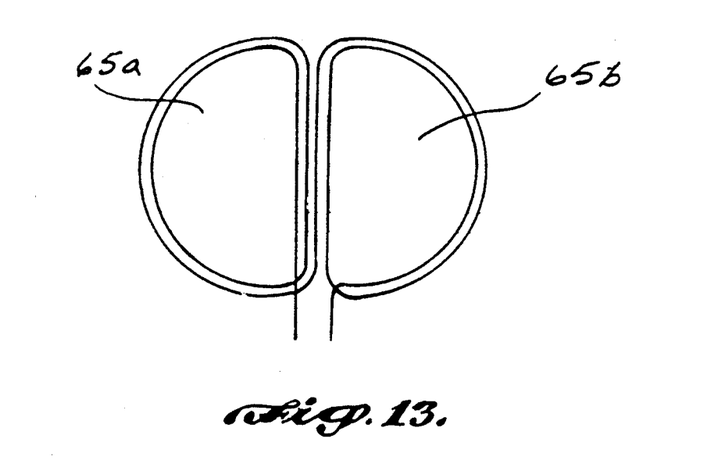
FIG. 13 is a wiring diagram of the embodiment of the invention illustrated in FIG. 12.

FIGS. 12-15 illustrate a splayed coil formed in accordance with the invention wherein the definable region of higher magnetic field intensity is created by winding density rather than mechanical shape. More specifically, FIG. 12 illustrates a splayed coil 61 positioned atop the cranium 63 of a patient. As best shown in FIG. 13, the splayed coil 61 includes two lobes 65a and 65b, each defined by a winding. The lobes are generally coplanar and each lobe 65a and 65b has a semicircular configuration. The lobes 65a and 65b are oriented such that they generally define a circle in their common plane.

Figure 14:
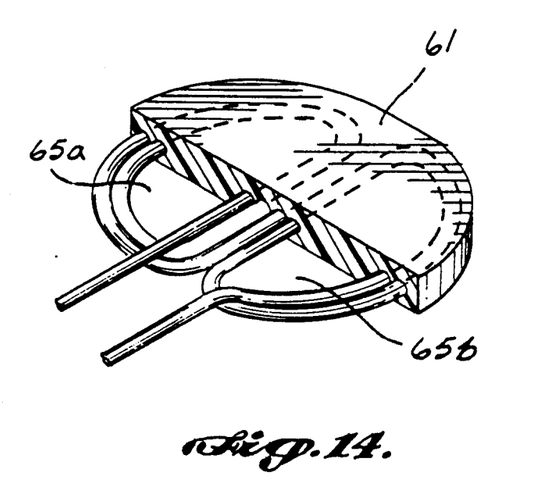
FIG. 14 is an enlarged, pictorial view, partially in section of the embodiment of the invention illustrated in FIGS. 12 and 13.
Figure 15:
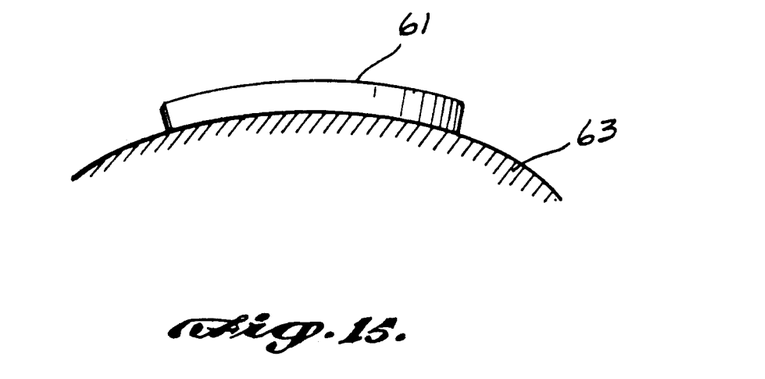
FIG. 15 is an edge view of a curved version of the embodiment of the invention illustrated in FIGS. 12–14.

As also illustrated in FIGS. 13 and 14, the coil 61 is wound such that the winding that defines one of the lobes 65a is first wound. After the first lobe 65a is wound, the second lobe 65b is wound. Rather than being precisely planar, the lobes 65a and 65b may be slightly curved to conform to the contour of the cranium 63 of a patient, as illustrated in FIG. 15. In the case of a curved configuration, the lobes are substantially flat, rather than being precisely flat.

In the case of the dual lobe splayed embodiment of the invention illustrated in FIGS. 12-15, the highest magnetic field concentration and, thus, the location beneath which neuron depolarization occurs, is where the concentration of wires is at a maximum, namely the longitudinal section of wires that is common to both lobes 65a and 65b.

As will be readily appreciated from the foregoing description, the invention provides magnetic stimulator coils. When placed on a patient's body and pulsed by a magnetic stimulator, the magnetic field produced by the coil depolarizes neurons underlying the region where the magnetic field produced by the coil is most intense and, thus, stimulates the related neural passageways of the patient. The focusability of coils formed in accordance with the invention, i.e., the ability to precisely position the coil atop the neural passageway to be stimulated, is substantially better than the focusability of prior art magnetic stimulator coils. Focusability is better because coils formed in accordance with the invention are designed to have increased magnetic field intensity either at a particular point, such as at a sharp corner, or along a short section of a coil. Coil efficiency is improved by splaying the windings of coils formed in accordance with the invention such that mutual inductance between windings is reduced in the region where the coil does not overlie the skin of a patient.

While preferred embodiments of the invention have been illustrated and described, it will be appreciated that various changes can be made therein without departing from the spirit and scope of the invention, as defined by the appended claims.

The embodiments of the invention in which an exclusive property or privilege is claimed are defined as follows:

1. A magnetic stimulator coil comprising a plurality of turns of electrical conductor wound into a geometric shape, said geometric shape including a straight section wherein all of the coil windings in said straight section lie parallel to one another and are more concentrated than in other sections of said geometric shape, said coil being wound such that when power is applied to said coil, the current flow through said more concentrated windings is in the same direction whereby the intensity of the magnetic field produced by said more concentrated windings as a result of said current flow through said more concentrated windings is greater than the intensity of the magnetic field produced in said other sections of said geometric shape as a result of said current flow through said other sections of said geometric shape.

2. A magnetic stimulator coil as claimed in claim 1, wherein said coil is generally flat and includes two separate, adjoining multi-turn lobes and wherein said straight section is located where said two lobes adjoin one another.

3. A magnetic stimulator coil as claimed in claim 1, wherein said windings are splayed in said other sections of said geometric shape.

4. A magnetic stimulator coil as claimed in claim 3, wherein said coil includes a corner, said corner forming a definable region.

5. A magnetic stimulator coil as claimed in claim 4, wherein said coil is petal-shaped.

6. A magnetic stimulator coil as claimed in claim 5, wherein the angle defined by the corner of said coil is acute.

7. A magnetic stimulator coil as claimed in claim 5, wherein the angle defined by the corner of said coil is a right angle.

8. A magnetic stimulator coil as claimed in claim 5, wherein the angle defined by the corner of said coil is obtuse.

9. A magnetic stimulator coil as claimed in claim 4, wherein said coil includes more than one corner.

* * * * *